(12) United States Patent
Dumeunier et al.

(10) Patent No.: US 8,519,152 B2
(45) Date of Patent: *Aug. 27, 2013

(54) PROCESS FOR THE PREPARATION OF PYRAZOLE CARBOXYLIC ACID AMIDES

(75) Inventors: Raphael Dumeunier, Stein (CH);
Florian Schleth, Munchwilen (CH);
Thomas Vettiger, Munchwilen (CH);
Michael Rommel, Munchwilen (CH);
Stephan Trah, Stein (CH)

(73) Assignee: Syngenta Crop Protection LLC, Greensboro, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/642,406

(22) PCT Filed: Apr. 14, 2011

(86) PCT No.: PCT/EP2011/055871
§ 371 (c)(1),
(2), (4) Date: Oct. 19, 2012

(87) PCT Pub. No.: WO2011/131545
PCT Pub. Date: Oct. 27, 2011

(65) Prior Publication Data
US 2013/0035496 A1 Feb. 7, 2013

(30) Foreign Application Priority Data

Apr. 20, 2010 (EP) .................................... 10160438

(51) Int. Cl.
*C07D 231/10* (2006.01)
*C07D 303/02* (2006.01)
*C07C 33/00* (2006.01)

(52) U.S. Cl.
USPC ................ 548/374.1; 549/544; 568/808

(58) Field of Classification Search
USPC ................ 548/374.1; 549/544; 568/808
See application file for complete search history.

(56) References Cited

FOREIGN PATENT DOCUMENTS
WO 2007/048556 5/2007
WO 2007/124907 11/2007

OTHER PUBLICATIONS

Hiroshi Tanida et al: Journal of the American Chemical Society, vol. 86, No. 22, Nov. 20, 1964, pp. 4904-4912.
International Search Report, International Application No. PCT/EP2011/055871, completion date: Jun. 14, 2011.

*Primary Examiner* — Samantha Shterengarts
(74) *Attorney, Agent, or Firm* — R. Kody Jones

(57) ABSTRACT

The invention relates to a process for the preparation of the compound of formula (I), which process comprises a) reacting a compound of formula (II), wherein X is chloro or bromo, with an organometallic species in an inert atmosphere to a halobenzyne of formula (X), reacting the halobenzyne of formula X so formed with cyclopentadiene to (III), b) reacting III in the presence of an inert solvent with an oxidant to (IV), c) reacting IV in the presence of a Lewis acid and a hydride source to (V), d) reacting V in the presence of an oxidizing agent, a base and an inert solvent to (VI), e) converting VI in the presence of a phosphane and $CCl_4$ or $CHCl_3$ to (VII), and either f1) reacting VII with $NH_3$ in the presence of a catalyst to the compound of formula (VIII); and g) reacting VIII in the presence of a base with a compound of formula (IX), to the compound of formula (I); or f2) reacting the compound of formula (VII), in the presence of a solvent, a base, a copper catalyst and at least one ligand with the compound of formula (IXa), to the compound of formula (I).

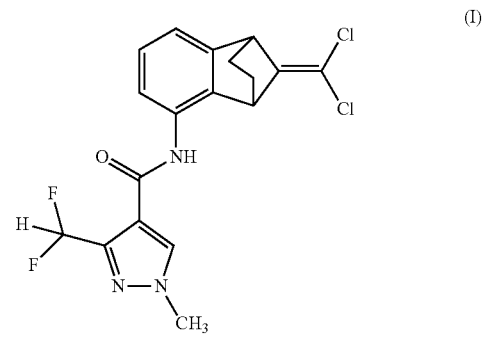

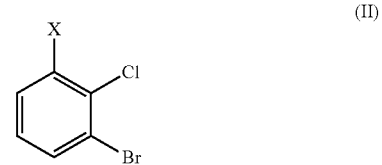

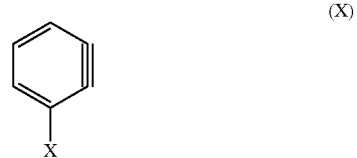

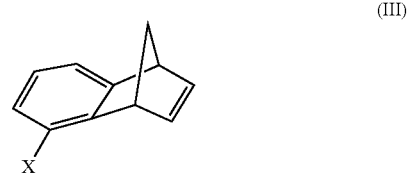

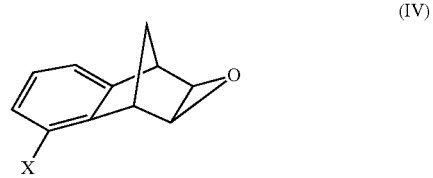

-continued
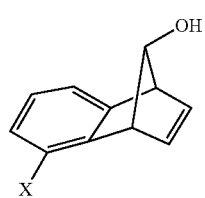
(V)
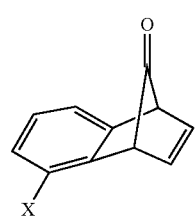
(VI)
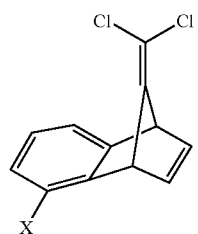
(VII)
-continued
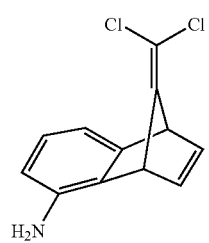
(VIII)
(IX)
8 Claims, No Drawings

PROCESS FOR THE PREPARATION OF PYRAZOLE CARBOXYLIC ACID AMIDES

This application is a 371 of International Application No. PCT/EP2011/055871 filed Apr. 14, 2011, which claims priority to EP 10160438.7 filed Apr. 20, 2010, the contents of which are incorporated herein by reference.

The present invention relates to a process for the preparation of 3-difluoromethyl-1-methyl-1H-pyrazole-4-carboxylic acid (9-dichloromethylene-1,2,3,4-tetrahydro-1,4-methano-naphthalen-5-yl)-amide and to novel intermediates useful for this process.

The compound 3-difluoromethyl-1-methyl-1H-pyrazole-4-carboxylic acid (9-dichloromethylene-1,2,3,4-tetrahydro-1,4-methano-naphthalen-5-yl)-amide and its microbicidal properties is described for example in WO 2007/048556.

The preparation of 3-difluoromethyl-1-methyl-1H-pyrazole-4-carboxylic acid (9-dichloromethylene-1,2,3,4-tetrahydro-1,4-methano-naphthalen-5-yl)-amide is known from WO 2007/048556. Said compound can be prepared according to schemes 1 and 4 by a) reacting the compound of formula A

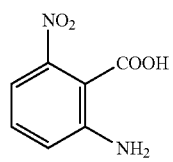
(A)

in the presence of an alkyl nitrite with a compound of formula B

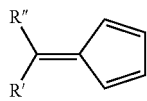
(B)

wherein R' and R" are e.g. $C_1$-$C_4$ alkyl, to a compound of formula C

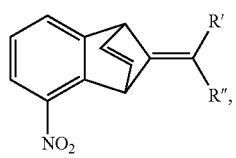
(C)

b) hydrogenating the compound of formula C in the presence of a suitable metal catalyst to a compound of formula D

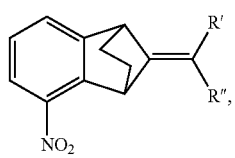
(D)

c) ozonising the compound of formula D and subsequent treatment with a reducing agent to a compound of formula E

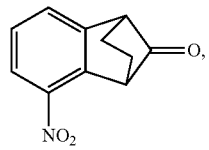
(E)

d) reacting the compound of formula E in the presence of triphenylphosphane/carbon tetrachloride to 2,9-dichloromethylidene-5-nitro-benzonorbornene of formula F

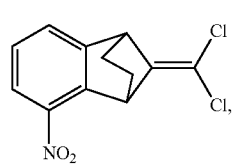
(F)

e) hydrogenating the compound of formula F in the presence of a metal catalyst to 2,9-dichloromethylidene-5-amino-benzonorbornene of formula G

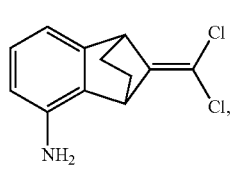
(G)

f) and reacting the compound of formula G with a compound of formula H

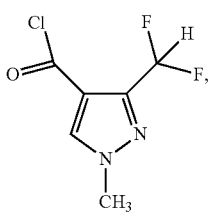
(H)

to 3-difluoromethyl-1-methyl-1H-pyrazole-4-carboxylic acid (9-dichloromethylene-1,2,3,4-tetrahydro-1,4-methano-naphthalen-5-yl)-amide.

A significant disadvantage of this prior art process is the ozonolysis reaction which is difficult to handle in large scale. Said disadvantage makes this process uneconomical and especially unsuitable for a large-scale production.

The aim of the present invention is therefore to provide a novel process for the production of 3-difluoromethyl-1-methyl-1H-pyrazole-4-carboxylic acid (9-dichloromethylene-1,2,3,4-tetrahydro-1,4-methano-naphthalen-5-yl)-amide that avoids the disadvantages of the known process and makes it possible to prepare 3-difluoromethyl-1-methyl-1H-pyrazole-4-carboxylic acid (9-dichloromethylene-1,2,3,4-tetrahydro-1,4-methano-naphthalen-5-yl)-amide in high yields and good quality in an economically advantageous way.

Thus, according to the present invention, there is provided a process for the preparation of the compound of formula I

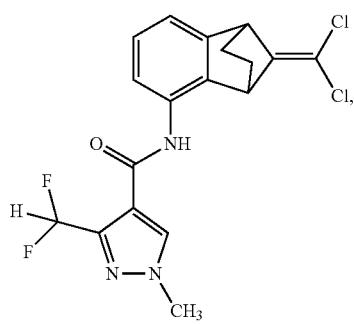
(I)

which process comprises
a) reacting a compound of formula II

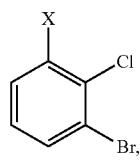
(II)

wherein X is chloro or bromo, with an organometallic species such as a $C_{1-6}$ alkyl- or phenyllithium or a $C_{1-6}$ alkyl- or a phenylmagnesium halide in an inert atmosphere to a halobenzyne of formula X

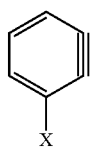
(X)

wherein X is chloro or bromo; reacting the halobenzyne of formula X so formed with cyclopentadiene to a compound of formula III

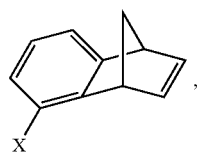
(III)

wherein X is chloro or bromo;
b) reacting the compound of formula III in the presence of an inert solvent with an oxidant to the compound of formula IV

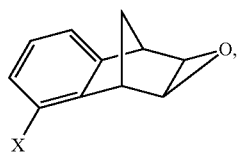
(IV)

wherein X is chloro or bromo;
c) reacting the compound of formula IV in the presence of a Lewis acid and a hydride source to the compound of formula V

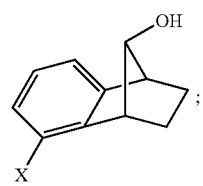
(V)

wherein X is chloro or bromo;
d) reacting the compound of formula V in the presence of an oxidizing agent, a base and an inert solvent to the compound of formula VI

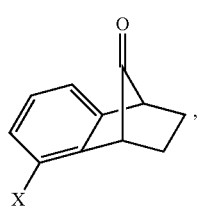
(VI)

wherein X is chloro or bromo;
e) converting the compound of formula VI in the presence of a phosphane and $CCl_4$ or $CHCl_3$, to the compound of formula VII

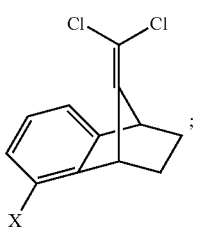
(VII)

wherein X is chloro or bromo; and either
f1) reacting the compound of formula VII with $NH_3$ in the presence of a catalyst comprising palladium and at least one ligand to the compound of formula VIII

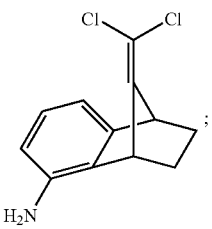
(VIII)

and g) reacting the compound of formula VIII in the presence of a base with a compound of formula IX

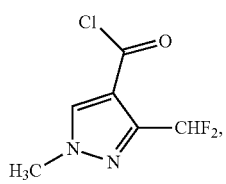

(IX)

to the compound of formula I; or f2) reacting the compound of formula VII

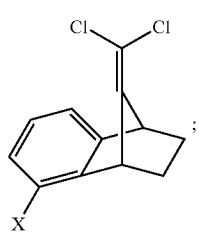

(VII)

wherein X is chloro or bromo, preferably bromo; in the presence of a solvent, a base, a copper catalyst and at least one ligand with the compound of formula IXa

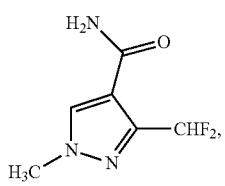

(IXa)

to the compound of formula I.

A further significant advantage of this invention over prior art processes is that the use of unstable dichlorofulvene is not necessary.

Reaction Step a):

The compound of formula II, wherein X is bromo, is known and disclosed, for example, in Recueil des Travaux Chimiques des Pays-Bas, 81, 365 (1962). The compound of formula II, wherein X is chloro or bromo, is disclosed, for example in WO 2008/049507. 1-bromo-2,3-dichloro-benzene may be prepared by the so-called Sandmeyer reaction from 2,3-dichloro-aniline. Such Sandmeyer reactions can be performed either by using an organic nitrite ester, such as tert-butyl nitrite or iso-pentyl nitrite, in an organic solvent, such as acetonitrile, in the presence of cupric bromide as brominating agent (as described in Journal of Organic Chemistry, 1977, 42, 2426-31) or by a two-step reaction involving diazotation in an acidic aqueous reaction media at temperatures of 0° C. to 15° C. using inorganic nitrite and then adding the reaction mixture to cuprous bromide solution (as described in Recueil des Travaux Chimiques des Pays-Bas et de la Belgique, 1932, 51, 98-113 and JP-6-2114-921). The compound of formula III may be prepared by a process which comprises reacting a halobenzyne of formula (X)

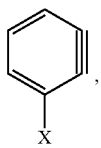

(X)

wherein X is chloro or bromo, with cyclopentadiene, in an inert organic solvent.

Depending on how the halobenzyne of formula X is generated, the process is carried out in an organic solvent such as tetrahydrofuran, 1,4-dioxane, dimethoxyethane, diethyl ether, tert-butyl methyl ether, methyl-ethyl-ketone, ethyl acetate, methylacetate or an aromatic or aliphatic hydrocarbon, for example, toluene, xylene, benzene, hexane, pentane or a petroleum ether, and at a temperature of from −20° C. to +10° C., which may be elevated to ambient temperature or to a higher temperature to complete the reaction.

The compound of formula (III) may be isolated by quenching the reaction mixture in an aqueous medium, for example, in saturated ammonium chloride solution, extracting the product in a solvent such as ethyl acetate, washing the solvent extract with, for example, brine and water, drying it and evaporating off the solvent to obtain the halobenzonorbornadiene (III), which may be further purified by crystallisation from a solvent such as hexane.

The halobenzyne (X) may be obtained by reacting the compound of formula II with an organometallic species in the presence of an inert solvent.

Preferred organometallic species for this reaction step are $C_{1-6}$ alkyl- or phenyllithium or $C_{1-6}$ alkyl- or phenylmagnesium halides. Isopropylmagnesium chloride is preferred.

The compound of formula III may be formed in a stepwise procedure, the halobenzyne (X) being formed in a first step and the compound of formula III being formed in a second step either by the subsequent addition of the cyclopentadiene or by the subsequent addition to the cyclopentadiene. The first step reaction between the halobenzene (II) with the organometallic species is carried out at a temperature of from −78° C. to 0° C., typically at −20° C. to −10° C. In the first case the subsequent cyclopentadiene addition is performed at temperatures of from −20° C. to +10° C., typically at −10° C. to 0° C. The reaction is promoted by warming the mixture to ambient temperature or preferably to the reflux temperature of the solvent used. In the second case the subsequent addition to the cyclopentadiene is carried out at 20° C. to 100° C., typically at 70° C. to 95° C. The reaction is stirred an additional hour to complete the conversion.

Suitable solvents include tetrahydrofuran, 1,4-dioxane, dimethoxyethane, diethyl ether, tert-butyl methyl ether, hexane, petroleum ethers, pentane, benzene, toluene and xylene, preferably toluene, tetrahydrofuran or hexane. The 5-chloro- or 5-bromobenzo-norbornadiene may then be isolated by quenching in an aqueous medium as described above.

The inert atmosphere in which the reaction is carried out is, for example, a nitrogen atmosphere. Transformations of this type are described by J. Coe in *Organic Letters*, 6, 1589 (2004) or P. Knochel in *Angew. Chem.* 116, 4464 (2004).

Reaction Step b):

Suitable oxidants are performic acid, peracetic acid or hydrogen peroxide in combination with an organic acid such as acetic acid. Carbamide peroxide in the presence of disodium hydrogen phosphate and acetic anhydride is also a suitable system for this oxidation. A preferred oxidant is meta-chloro-perbenzoic acid. Suitable solvents for reaction step b) are for example chloroform, acetonitrile, tetrahydrofurane, dichloromethane, dimethoxyethane or dioxane. Dichloromethane is preferred. The reaction can be performed at a temperature from 0° C. to the refluxing temperature of the solvent, preferably at 20-30° C.

The compound of formula IV is novel, is especially developed for the process according to the invention and therefore constitutes a further object of the invention.

Reaction Step c):

In order to open this epoxide, rearrange and reduce the carbocation formed from the opening, a combination of Lewis acid and hydride source can be used, such as $BH_3.DMS$ or $BH_3.THF$ (playing the role of Lewis acid, 1.2-1.4 eq.) and $NaBH_4$ or $LiAlH_4$ (catalytic, 0.1-0.2 eq., as they can be regenerated in situ from the boron alkoxide formed during the first steps). Another method is to use a reducing agent which is also a Lewis acid, such as DiBAl—H. Another possibility is $LiAlH_4$ alone, as it generates in situ Al(III) species which are Lewis acidic.

Preferred solvents are THF, $Et_2O$, toluene, depending on the reagents used. The temperature can vary from −78° C. to reflux. Preferred method is the use of $LiAlH_4$ in refluxing $Et_2O$.

The compound of formula V is novel, is especially developed for the process according to the invention and therefore constitutes a further object of the invention.

Reaction Step d):

Methods to oxidise a secondary alcohol to a ketone are described in the prior art, most of them would be suited for this particular transformation.

The mild Swern oxidation is a chemical reaction whereby a primary or secondary alcohol is oxidized to an aldehyde or ketone using oxalyl chloride for the activation of the oxidizing agent, which is in particular dimethyl sulfoxide in the presence of an organic base, such as triethylamine. It can be performed in inert solvents such as chlorinated alkanes, and the temperature has to be maintained preferably between −78° C. and −55° C. before the final addition of the base.

Reaction Step e):

The compounds of formula VII are obtained by the Wittig olefination of the compounds of formula VI with in situ generated dihalomethylidene phosphoranes RP=C(Cl)Cl, where R is triphenyl, tri $C_{1-4}$ alkyl or tridimethylamine, according to or by analogy with the procedures described by H-D. Martin et al, *Chem. Ber.* 118, 2514 (1985), S. Hayashi et al, *Chem. Lett.* 1979, 983, or M. Suda, *Tetrahedron Letters*, 22, 1421 (1981).

Suitable solvents are for example acetonitrile or $CH_2Cl_2$, preferred is acetonitrile.

The temperature can vary between ambient temperature and 60° C., preferred is a range of 50-60° C., in particular 60° C. A preferred phosphane is triphenylphosphane which can be used in an amount of 2.2-8 eq., preferred 2.2 eq. The carbon tetrachloride can be used in an amount of 1.5-5eq, preferred 1.5 eq. The ratio $CCl_4$:$PPh_3$ is 1:2 up to 1:1.7. The reaction can also be performed with chloroform instead of carbon tetrachloride. Carbon tetrachloride is preferred.

The compound of formula VII is novel, is especially developed for the process according to the invention and therefore constitutes a further object of the invention.

Reaction Step f1):

From the two process variants step f1) to step g) and step f2), the variant step f1) to g) is preferred. The catalyst which comprises palladium and at least one ligand used in the process will generally be formed from a palladium precursor and at least one suitable ligand. Where the process is carried out in a solvent, the complex will normally be soluble in the solvent. In the context of this process palladium complexes expressly include those consisting of cyclic organic palladium compounds ("palladacycles") and secondary phosphane ligands.

The palladium complex may be used as a robust, preformed species or may be formed in situ. Typically it is made by reacting a palladium precursor with at least one suitable ligand. In the case of incomplete transformations, residual amounts of the palladium precursor or ligand may be present undissolved in the reaction mixture.

Useful palladium precursors may be chosen from palladium acetate, palladium chloride, palladium chloride solution, palladium$_2$-(dibenzylidene acetone)$_3$ or palladium-(dibenzylidene acetone)$_2$, palladium-tetrakis (triphenylphosphane), palladium/carbon, palladium dichloro-bis(benzonitrile), palladium-(tris-tert-butylphosphane)$_2$ or a mixture of palladium$_2$-(dibenzylidene acetone)$_3$ and palladium-(tris-t-butylphosphane)$_2$.

Useful ligands are, for example, tertiary phosphane ligands, N-heterocyclic carbene ligands and phosphanic acid ligands. Tertiary phosphane ligands are generally of two types: monodentate and bidentate ligands. A monodentate ligand may occupy one palladium coordination site while a bidentate ligand occupies two coordination sites and hence is able to chelate the palladium species.

The following are examples of tertiary phosphane, N-heterocyclic carbene and phosphanic acid ligands and a palladacycle with a secondary phosphane ligand.

(A) Monodentate phosphane ligands:

Tri-tert-butylphosphane, tri-tert-butylphosphonium tetrafluoroborate ("P(tBu)$_3$HBF$_4$"), tris-ortho-tolylphosphane ("P(oTol)$_3$"), tris-cyclohexylphosphane ("P(Cy)$_3$"), 2-di-tert-butyl-phosphano-1,1'-bisphenyl ("P(tBu)$_2$BiPh"), 2-dicyclohexyl-phosphano-1,1'-bisphenyl ("P(Cy)$_2$BiPh"), 2-dicyclohexylphosphano-2',4',6'-tri-isopropyl-1,1'-bisphenyl ("x-Phos"), and tert-butyl-di-1-adamantyl-phosphane ("P(tBu)(Adam)$_2$").

More information about monodentate phosphane ligands can be found in US-2004-0171833.

(B) Bidentate tertiary phosphane ligands:

(B1) Biphosphane ligands:

(B1.1) Ferrocenyl-Biphosphane ligands ("Josiphos" ligands):

1,1'-bis(diphenylphosphano)ferrocene (dppf), 1,1'-bis(di-tert-butylphosphano)-ferrocene, (R)-(−)-1-[(S)-2-(bis(4-trifluoromethylphenyl)phosphano)ferrocenyl]ethyl-di-tert-butyl-phosphane, (R)-(−)-1-[(S)-2-(di(3,5-bis-trifluoromethylphenyl)phosphano)ferrocenyl]ethyl-dicyclohexylphosphane, (R)-(−)-1-[(S)-2-(di(3,5-bis-trifluoromethylphenyl)phosphano)-ferrocenyl]ethyldi(3,5-dimethylphenyl)phosphane, (R)-(−)-1-[(S)-2-(dicyclohexylphosphano)-ferrocenyl]ethyldi-tert-butylphosphane, (R)-(−)-1-[(S)-2-(dicyclohexylphosphano)ferrocenyl]-ethyldicyclohexylphosphane, (S)-(+)-1-[(R)-2-(dicyclohexylphosphano)ferrocenyl]ethyl-dicyclohexylphosphane, (S)-(+)-1-[(R)-2-(dicyclohexylphosphano)ferrocenyl]ethyldiphenyl-phosphane, (R)-(−)-1-[(S)-2-(bis(3,5-dimethyl-4-methoxyphenyl)phosphano)ferrocenyl]-ethyldicyclohexylphosphane, (S)-(+)-1-[(R)-2-(di-furylphosphano)ferrocenyl]ethyldi-3,5-xylyl-phosphane, (R)-(−)-1-[(S)-2-(diphenylphosphano)ferrocenyl]ethyldi-tert-butylphosphane, (S)-(+)-1-[(R)-2-(diphenylphosphano) ferrocenyl]ethyldi-tert-butylphosphane, (R)-(−)-1-[(S)-2-(diphenylphosphano)ferrocenyl] ethyldicyclohexylphosphane, (R)-(+)-1-[(R)-2-(diphenyl-phosphano)ferrocenyl]ethyldicyclohexylphosphane, (S)-(+)-1-[(R)-2-(diphenylphosphano)-ferrocenyl] ethyldicyclohexylphosphane, (R)-(−)-1-[(S)-2-(dicyclohexylphosphano)ferrocenyl]-ethyldiphenylphosphane, (R)-(−)-1-[(S)-2-(diphenyl) phosphano)ferrocenyl]ethyldi(3,5-dimethylphenyl) phosphane, (R)-(−)-1-[(S)-2-(di-tert-butyl-phosphano) ferrocenyl]ethyl-di-o-tolylphosphane

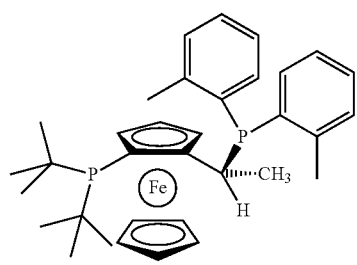

(R)-(−)-1-[(S)-2-(bis(3,5-dimethyl-4-methoxyphenyl)phosphano)ferrocenyl]-ethyl-di-tert-butylphosphane

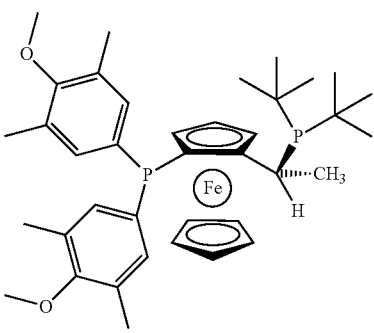

(R)-(−)-1-[(S)-2-(diethylphosphano)ferrocenyl]-ethyl-di-tert-butylphosphane

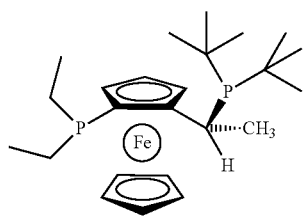

(R)-(−)-1-[(S)-2-(P-methyl-P-isopropyl-phosphano)ferrocenyl]ethyldicyclohexylphosphane

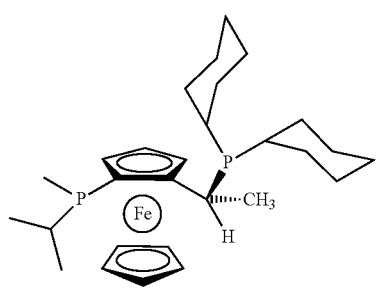

(R)-(−)-1-[(S)-2-(P-methyl-P-phenyl-phosphano)ferrocenyl]ethyl-di-tert-butylphosphane

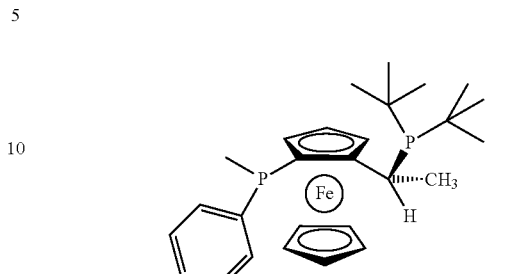

and racemic mixtures thereof, especially racemic mixtures of 1-[2-(di-tert-butylphosphano)-ferrocenyl]ethyl-di-o-tolylphosphane, 1-[2-(dicyclohexylphosphano)ferrocenyl]ethyldi-tert-butylphosphane and 1-[2-(diphenylphosphano)ferrocenyl]ethyldicyclohexylphosphane.

(B1.2) Binaphthyl-bisphosphane ligands:

2,2'bis(diphenylphosphano)-1,1'-binaphthyl ("BI NAP"), R-(+)-2,2'-bis(di-p-tolylphosphano)-1,1'-binaphthyl ("Tol-BINAP"), racemic 2,2'-bis(di-p-tolylphosphano)-1,1'-binaphthyl ("racemic Tol-BINAP").

(B1.3) 9,9-Dimethyl-4,5-bis(diphenyl-phosphano)-xanthene ("Xantphos").

(B2) Aminophosphane2 ligands:

(B2.1) Biphenyl ligands:

2-dicyclohexylphosphano-(N,N-dimethylamino)-1,1'-biphenyl ("PCy$_2$NMe$_2$BiPh")

2-di-tert-butylphosphano-(N,N-dimethylamino)-1,1'-biphenyl ("P(tBu)$_2$NMe$_2$BiPh").

(C) N-Heterocyclic carbene ligands:

1,3-bis-(2,6-diisopropylphenyl)-imidazolium chloride ("I-Pr"), 1,2-bis(1-adamantyl)-imidazolium chloride ("I-Ad") and 1,3-bis-(2,6-methylphenyl)-imidazolium chloride ("I-Me").

(D) Phosphanic acid ligands:

di-tert-butyl-phosphanoxide.

(E) Palladacycles containing a secondary phosphane ligand:

the complex of the formula (A-1)

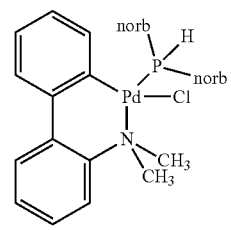

(A-1)

where "norb" is norbornyl, and the complex of the formula (A-2)

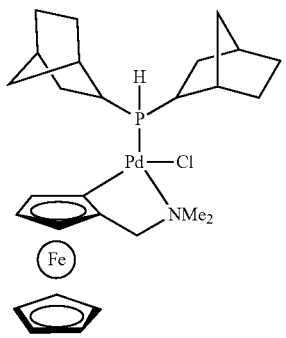

(A-2)

The palladium complex (A-1) is described in *Synlett.*, 2549-2552 (2004) under the code name "SK-CC01-A". The complex (A-2) is described in *Synlett.* (ibid) under the code name "SK-0002-A".

Further examples of palladium complexes containing phosphanic acid ligands are described in *J. Org. Chem.* 66, 8677-8681 under the code names "POPd", "POPd2" and "POPD1".

Further examples of palladium complexes containing N-heterocyclic carbene ligands are naphthoquinone-1,3-bis (2,6-diisopropylphenyl)imidazole-2-ylidene-palladium (["Pd—NQ—IPR]$_2$"), divinyl-tetramethylsiloxane-1,3-bis(2, 6-diisopropylphenyl)imidazole-2-ylidene-palladium ("Pd—VTS—IPr"), 1,3-bis(2,6-diisopropylphenyl)imidazole-2-ylidene-palladium dichloride ("Pd—Cl—IPr"), 1,3-bis(2,6-diisopropylphenyl)imidazole-2-ylidene-palladium diacetate ("Pd—OAc—IPr"), allyl-1,3-bis(2,6-diisopropylphenyl) imidazole-2-ylidene-palladium chloride ("Pd—Al—Cl—IPr") and a compound of the formula (A-3):

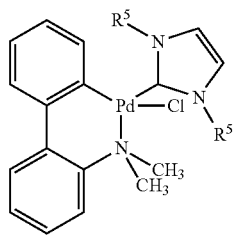

(A-3)

where $R^5$ is 2,6-diisopropylphenyl or 2,4,6-trimethylphenyl. More information about [Pd—NQ—IPR]$_2$, Pd—VTS—IPr, Pd—Cl—IPr, Pd—OAc—IPr and Pd—Al—Cl—IPr can be found in *Organic Letters*, 4, 2229-2231 (2002) and *Synlett.*, 275-278, (2005). More information about the compound of formula (A-3) can be found in *Organic Letters*, 5, 1479-1482 (2003).

A single palladium complex or a mixture of different palladium complexes may be used in the process for preparing the compound of the general formula (VIII).

Palladium precursors that are particularly useful for the formation of the palladium complexes are those selected from palladium acetate, palladium$_2$-(dibenzylidene acetone)$_3$, palladium-(dibenzylidene acetone)$_2$, palladium chloride solution or a mixture of palladium$_2$-(dibenzylidene acetone)$_3$ and palladium-(tris-tert.-butylphosphane)$_2$. Palladium acetate is especially useful, as is palladium chloride.

At least one ligand is used for the formation of the palladium complex. Normally the palladium complex will have at least one ligand chosen from a monodentate tertiary phosphane ligand, a bidentate teritary phosphane ligand and a N-heterocyclic carbene ligand, and typically at least one ligand chosen from a ferrocenyl-biphosphane ligand, a binaphthyl-bisphosphane ligand and an aminophosphane ligand.

Particularly suitable are palladium complexes that contain at least one ligand selected from tri-tert-butylphospine, P(tBu)$_3$HBF$_4$, P(oTol)$_3$, P(Cy)$_3$, P(tBu)$_2$BiPh, P(Cy)$_2$BiPh, x-Phos, P(tBu)(Adam)$_2$, (R)-(−)-1-[(S)-2-(dicyclohexylphosphano)ferrocenyl]ethyldi-tert-butylphosphane, racemic 1-[2-(dicyclohexylphosphano)ferrocenyl]ethyldi-tert-butylphosphane, (R)-(−)-1-[(S)-2-(di-tert-butyl-phosphano) ferrocenyl]ethyldi-o-tolylphosphane, racemic 1-[2-(di-tert-butyl-phosphano)ferrocenyl]ethyldi-o-tolylphosphane, dppf, 1,1'-bis(di-tert-butyl-phosphano)-ferrocene, (R)-(−)-1-[(S)-2-(diphenylphosphano)ferrocenyl]ethyldicyclohexylphosphane, racemic 1-[2-(diphenylphosphano)ferrocenyl]ethyldicyclohexylphosphane, (R)-(−)-1-[(S)-2-(diphenylphosphano)ferrocenyl]ethyldi-tert-butylphosphane, BINAP, Tol-BINAP, racemic Tol-BINAP, Xantphos, PCy$_2$NMe$_2$BiPh, P(tBu)$_2$NMe$_2$BiPh, I—Pr, I-Ad and I-Me, and a palladium complex of formula (A-3), where $R^5$ is 2,6-diisopropylphenyl or 2,4,6-trimethyl-phenyl.

Preferred are palladium complexes with at least one ligand selected from tri-tert-butylphospine, P(tBu)$_3$HBF$_4$, P(tBu)$_2$BiPh, P(Cy)$_2$BiPh, x-Phos, (R)-(−)-1-[(S)-2-(dicyclohexylphosphano)ferrocenyl]ethyldi-tert-butylphosphane, racemic 1-[2-(dicyclohexylphosphano)ferrocenyl]ethyldi-tert-butylphosphane, (R)-(−)-1-[(S)-2-(di-tert-butyl-phosphano) ferrocenyl]ethyldi-o-tolylphosphane, racemic 1-[2-(di-tert-butyl-phosphano)ferrocenyl]ethyldi-o-tolylphosphane, dppf, PCy$_2$NMe$_2$BiPh and I—Pr.

Of especial interest are palladium complexes that contain at least one ligand selected from the following groups:
(i) tri-tert-butylphospine, P(tBu)$_3$HBF$_4$, P(tBu)$_2$BiPh, P(Cy)$_2$ BiPh, x-Phos, PCy$_2$NMe$_2$BiPh and I—Pr;
(ii) tri-tert-butylphospine, P(tBu)$_3$HBF$_4$, PCy$_2$NMe$_2$BiPh and I—Pr;
(iii) tri-tert-butylphospine and P(tBu)$_3$HBF$_4$; and
(iv) (R)-(−)-1-[(S)-2-(dicyclohexylphosphano)ferrocenyl] ethyldi-tert-butylphosphane and racemic 1-[2-(dicyclohexylphosphano)ferrocenyl]ethyldi-tert-butylphosphane.

Preferred are palladium complexes that contain as a ligand PCy$_2$NMe$_2$BiPh, I—Pr, (R)-(−)-1-[(S)-2-(dicyclohexylphosphano)ferrocenyl]ethyldi-tert-butylphosphane or racemic 1-[2-(dicyclohexylphosphano)ferrocenyl]ethyldi-tert-butylphosphane.

A preferred complex is one where the precursor is palladium chloride and the ligand is (R)-(−)-1-[(S)-2-(dicyclohexylphosphano)ferrocenyl]ethyldi-tert-butylphosphane.

The palladium complex is used in the preparation of the compound of formula (II) in a catalytic amount, normally in a molar ratio of from 1:10 to 1:10000 in respect to the compound of formula (IV), typically in a ratio of 1:100 to 1:1000, for example, 1:500 to 1:700 or about 1:600. The complex may be pre-formed or formed in situ by mixing together the precursor and ligand, which will generally be used in equimolar amounts, or thereabouts.

An especially preferred palladium catalyst for reaction step f) is Pd(OAc)$_2$ (preferred loading is 3-5 mol %, in particular 4 mol %), a ligand selected from the Josiphos, DavePhos (e.g. 2-dicyclohexylphosphano-2'-(N,N-dimethylamino)biphenyl) or Xantphos 4,5-Bis(diphenylphosphano)-9,9-dimethylxanthene) types, preferred is the Josiphos type, in particular Josiphos SL-J009-1 which is (2R)-1-[(1R)-1-[bis(1,1-dimethylethyl)phosphano]ethyl]-2-(dicyclohexylphosphano) ferrocene (preferred amount is 3-5 mol %, in particular 4.4 mol %).

NH$_3$ is advantageously added under a pressure of 0.9 to 1.1 MPa, preferably 1 to 1.05 MPa. The reaction step is preferably performed at temperatures from 80 to 150° C., preferably 100 to 120° C. at pressures from 1.4 to 2.6 MPa, preferably 1.5 to 2.2 MPa, in particular 2.2 MPa. Preferred solvents are ethers like dimethylether.

Reaction Step g):

The compound of formula IX is known and is disclosed, for example, in U.S. Pat. No. 5,093,347.

Preferred bases for reaction step g) are amines like triethylamine, or sodium or potassium carbonate or bicarbonate, or NaOH, preferably triethylamine or NaOH.

Preferred solvents are xylene, toluene or chlorobenzene. The reaction is preferably performed at temperatures from −10 to 90° C., preferably from 70 to 80° C.

Reaction Step f2):

The compound of formula IXa is for example described in PCT/EP2009/067286.

The reaction step f2) can be performed at temperatures from 100 to 180° C., preferably at 130° C. Heating is possible in a sealed vial, open flask, under reflux or under microwave irradiation, preferably in a sealed vial.

As solvents can be used amides (DMF, NMP), alcohols (cyclohexanol), ethers (diglyme, dioxane), sulfoxides (DMSO), hydrocarbons (mesitylene, toluene), nitriles (butyronitrile) and mixtures thereof (toluene/methanol, toluene/cyclohexanol, dioxane/methanol, dioxane/water), preferably toluene and dioxane.

As copper sources can be used Cu(0), Cu(I) or Cu(II) salts. Examples are Cu(0) powder, Cu(I) iodide, Cu(I) thiophenecarboxylate, Cu(II) phthalocyanine, Cu(II) acetate, Cu(II) oxide, Cu(II) chloride, Cu(II) bromide, Cu(II) sulfate pentahydrate and mixtures thereof, preferably Cu(II) oxide and Cu(II) chloride.

The copper catalyst can be used in amounts between 2 and 330 mol-%, preferably 8-12 mol-%, in particular 10 mol-%. If Cu(0) is used, the amount is preferably >100 mol %.

Ligands are generally required for effective catalysis. Examples are N,N'-dimethylethylenediamine, 1,2-bisdimethylaminocyclohexane, 1,2-diaminocyclohexane, 1,2-phenylenediamine, 4-dimethylaminopyridine, 1,2-bis(3-aminopropylamino)ethane, triethylenetetramine, diethylenetriamine, Tris(2-aminoethyl)amine. Preferably, N,N'-dimethylethylenediamine is used. Carbonates can be used as the base, for example cesium carbonate and preferably potassium carbonate. The conversion is generally completed after 5-24 hours.

PREPARATORY EXAMPLES

Step a): Preparation of 5-chloro-1,4-dihydro-1,4-methano-naphthalene of formula IIIa

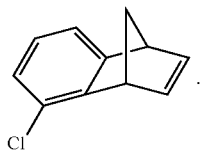

(IIIa)

115 g of 1-Bromo-2,3-dichlorobenzene was dissolved in 470 g of toluene and the solution was cooled down to −10° C. Then a 20% THF solution of isopropylmagnesium chloride (309 g) was added over 30 min and the reaction mixture was stirred 1 hour at −10° C. Freshly distilled cyclopentadiene (44.5 g, 1.3 eq) was added over 10 min. After one hour stirring at ambient temperature, the mixture was heated to reflux. When the conversion was completed, the reaction mixture was filtered off and washed twice with toluene. The mother liquor was evaporated and 106 g of brown crude oil was obtained (yield: 91.5%. The material can be purified by distillation or by CC (silica gel, eluant: Hept/TBME 19/1).

$^1$H-NMR (400 MHz, CDCl$_3$): δ=7.08-6.97 (m, 3H, Ar—H); 7.00-6.96 (m, 2H, Vinyl-H); 4.32-4.31 (m, 1H); 4.09-4.08 (m, 1H); 2.46 (dt, J=7.5 Hz, 1.5 Hz, 1H); 2.41 (dt, J=7.0 Hz, 1.5 Hz, 1H).

Step b): Preparation of the Compound of Formula IVa

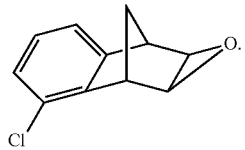

(IVa)

10.6 g of 5-Chloro-1,4-dihydro-1,4-methano-naphthalene was dissolved in 200 ml of CH$_2$Cl$_2$ and cooled down to 0° C. 15 g meta-chloro-perbenzoic acid diluted in 160 ml CH$_2$Cl$_2$ was added over 10 min and the reaction mixture was stirred at ambient temperature until complete conversion of the starting-material. Sodium hydrogen sulfite solution was added to the reaction mixture and the organic phase was separated. The organic phase was washed twice with NaHCO$_3$ solution then with brine. After solvent evaporation, 12 g of viscous yellow crude product was obtained (yield: quantitative). After purification (CC, silica gel, eluant: 19/1 Hept/EA) the compound could be obtained in form of a white solid.

$^1$H-NMR (400 MHz, CDCl$_3$): δ=7.05-7.03 (m, 1H, Ar—H); 6.97-6.89 (m, 2H, Ar—H); 3.62-3.61 (m, 1H); 3.39-3.37 (m, 2H); 3.31-3.30 (m, 1H); 2.19-2.11 (m, 2H); 1.89 (dt, J=9.2 Hz, 1.7 Hz, 1H); 1.47 (dt, J=8.8 Hz, 1.1 Hz, 1H).

Step c): Preparation of 5-chloro-1,2,3,4-tetrahydro-1,4-methano-naphthalen-9-ol of Formula Va

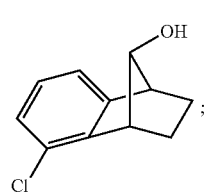

(Va)

Example with LiAlH$_4$

In a dry vial and at ambient temperature, 28 mg of LiAlH$_4$ (0.78 mmol, 1 eq.) was stirred in 1 ml of Et$_2$O. To this mixture, a solution of the compound of formula IVa (150 mg, 0.78 mmol, 1 eq.) in 4 ml of Et$_2$O was added slowly. The resulting mixture was heated to reflux during 16 hours, then it was allowed to cool down to ambient temperature. An aqueous saturated solution of ammonium chloride was then added carefully. The two phases were then separated, the aqueous layer was extracted with ethyl acetate, the combined organic layers were washed with saturated aqueous ammonium chloride, dried over solid sodium sulphate and concentrated under vacuum. The crude product was then purified by chromatography column on silica gel, eluting with heptanes/ethyl acetate 4/1. 105 mg of the compound of formula Va was obtained (70% yield).

Example with diisobutyl-aluminiumhydride 0.6 g of the compound of formula IVa was dissolved under argon atmosphere in 5 g toluene. The mixture was cooled down to 0° C. and 2.5 g diisobutyl-aluminiumhydride (1 eq) was added over 1 hour at 0° C. The reaction mixture was stirred until constant amount of product formed. The reaction mixture was diluted with AcOEt, and then extracted with cold acidic water, water and brine. The obtained crude oil was purified with chromatography (Heptane/AcOEt: 4/1). Yield: 50%

$^1$H-NMR (400 MHz, CDCl$_3$): 7.13-7.05 ppm (3H, m); 3.87 ppm (1H, bs); 3.41 ppm (1H, bs); 3.19 ppm (1H, bs); 2.15 ppm, (2H, m); 1.79 ppm (1H, d, J=4 Hz); 1.32-1.15 ppm (2H, m).

Step d): Preparation of 5-chloro-1,2,3,4-tetrahydro-1,4-methano-naphthalen-9-one of Formula VIa

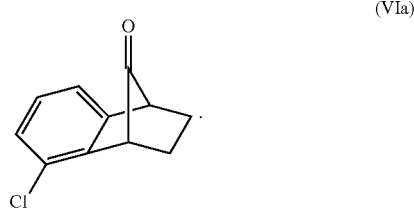 [SMILES: O=C1C2CCC1c1c(Cl)cccc12]

(VIa)

1.8 g of oxalyl chloride (6.1 eq) was dissolved in 35 ml of CH$_2$Cl$_2$ and cooled down to −60° C. To this solution, the following reagents were added one after the other: 1/2.2 g of DMSO (12.2 eq) dissolved in 10 ml CH$_2$Cl$_2$ over 5 min; 2/460 mg of the compound of formula Va dissolved in 10 ml CH$_2$Cl$_2$ over 5 min and the mixture was stirred 15 min; 3/6.65 g triethylamine (27.8 eq) diluted in 10 ml CH$_2$Cl$_2$ and the mixture was stirred 5 min. After completion of addition, the mixture was self-heated to ambient temperature. The reaction mixture was diluted with CH$_2$Cl$_2$ then washed with water and brine. The organic phase was distilled off to give 0.7 g of crude viscous oil. The product was purified via flash-chromatography (Heptane/AcOEt: 95/5). 0.4 g pure material was obtained=>yield: 88%

$^1$H-NMR (400 MHz, CDCl$_3$): δ=7.25-7.17 (m, 3H, Ar—H); 3.61-3.60 (m, 1H); 3.41-3.40 (m, 1H); 2.27-2.21 (m, 2H); 1.47-1.36 (m, 2H).

Step e): Preparation of 5-chloro-9-dichloromethylene-1,2,3,4-tetrahydro-1,4-methano-naphthalene of Formula VIIa

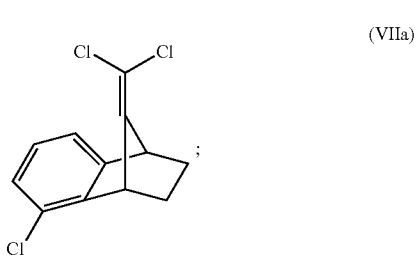 [SMILES: ClC(Cl)=C1C2CCC1c1c(Cl)cccc12]

(VIIa)

To a solution of 50 g of 5-chloro-1,2,3,4-tetrahydro-1,4-methano-naphthalen-9-one and 520 ml acetonitrile, 157 g (2.2 eq) PPh$_3$ was added in portion at ambient temperature. Then 60 g CCl$_4$ (1.5 eq) were feed over 40 min. The reaction mixture was heated at 60° C. and stirred until complete conversion. The reaction mixture was distilled off to give 259 g crude oil.

500 g ice water and 500 ml CH$_2$Cl$_2$ were added. After phase separation, the aqueous phase was washed with CH$_2$Cl$_2$. The combined organic phases were washed with brine and the organic phases distilled off.

To purify the crude oil, 400 ml acetone was added and the oil was dissolved at 50° C. By adding 500 ml hexane, product was precipitated. The product was filtered off and washed with 150 ml hexane. The mother liquor was evaporated and recrystallised as described previously; this operation was repeated twice. In total, 66.1 g brown oil was obtained; this latter was purified over silica (AcOEt/cyclohexane: 1/9) to give 62.8 g of the compound of formula VIIa. Yield: 93.2%.

$^1$H-NMR (400 MHz, CDCl$_3$): δ=7.13-7.03 (m, 3H, Ar—H); 4.18-4.17 (m, 1H); 3.97-3.96 (m, 1H); 2.15-2.07 (m, 2H); 1.45-1.32 (m, 2H).

Step f1): Preparation of 9-dichloromethylene-1,2,3,4-tetrahydro-1,4-methano-naphthalen-5-ylamine of formula VIII starting from 5-bromo-9-dichloromethylene-1,2,3,4-tetrahydro-1,4-methano-naphthalene

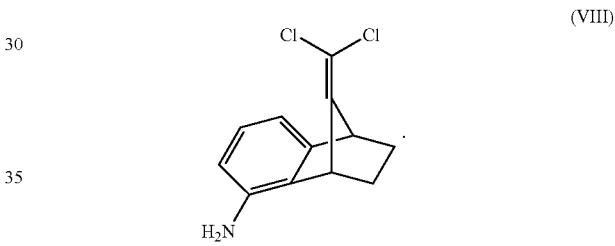

(VIII)

Catalyst Preparation 8.98 mg of palladium acetate (0.040 mmol) and 22 mg of Josiphos Ligand (Josiphos SL-J009-1, (2R)-1-[(1R)-1-[bis (1,1-dimethylethyl)phosphano]ethyl]-2-(dicyclohexylphosphano)ferrocene (Solvias AG), 0.040 mmol) were placed in a 5 ml Schlenk tube and inertized with Argon/Vacuum. 2.5 ml dimethylether was added and the catalyst was left stirring for 15 min.

Starting-Material Solution 608 mg of 5-bromo-9-dichloromethylene-1,2,3,4-tetrahydro-1,4-methano-naphthalene (2 mmol) was placed in a 5 ml Schlenk tube and inertized with argon/vacuum. 2.5 ml degassed dimethylether was then added to the starting material.

Reaction 384 mg of NaOtBu (4 mmol) was placed in the stainless steel 50 ml autoclave.

The autoclave was screwed on and set under argon. Under a constant flow of argon, the starting material solution was transferred into the autoclave, followed by the catalyst solution. NH$_3$ was added until pressure reached 1.05 MPa. The autoclave was heated to 105° C., pressure increased to 1.6

MPa. After 32 hour reaction, the reaction was stopped. 79% product was identified by HPLC.

The compound of formula VIII can be prepared analogously with 5-chloro-9-dichloromethylene-1,2,3,4-tetrahydro-1,4-methano-naphthalene as starting material.

Step g): Preparation of 3-difluoromethyl-1-methyl-1H-pyrazole-4-carboxylic acid (9-dichloromethylene-1,2,3,4-tetrahydro-1,4-methano-naphthalen-5-yl)-amide of formula I

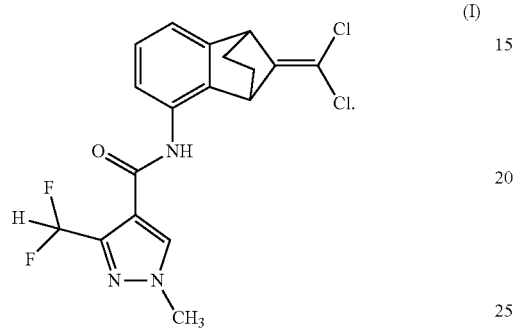

9-Dichloromethylene-1,2,3,4-tetrahydro-1,4-methano-naphthalen-5-ylamine (166 g, 35% xylene solution, 0.25 mol), triethylamine (28 g, 0.275 mol) and xylene (13 g) were charged in a reactor and the mixture was heated to 80° C. 3-Difluoromethyl-1-methyl-1H-pyrazole-4-carbonyl chloride (182 g, 26% xylene solution, 0.25 mol) was added over 2 hours. After conversion, the product was extracted, concentrated and crystallized in a mixture of xylene/methycyclohexane. 83 g of pure product were isolated. (Purity: 97%, Yield: 82%)

$^1$H-NMR (400 MHz, CDCl$_3$): δ=8.12 (bs, 1H, NH); 8.05 (s, 1H, Pyr—H); 7.83-7.80 (d, 1H, Ar—H); 7.19-7.15 (t, 1H, Ar—H); 7.04 (d, 1H, Ar—H); 7.02-6.76 (t, 1H, CHF$_2$); 4.1 (s, 1H, CH); 3.95-4.0 (bs, 4H, CH & CH$_3$); 2.18-2.08 (m, 2H, CH$_2$); 1.55-1.3 (2m, 2H, CH$_2$).

Step f2): Preparation of 3-difluoromethyl-1-methyl-1H-pyrazole-4-carboxylic acid (9-dichloromethylene-1,2,3,4-tetrahydro-1,4-methano-naphthalen-5-yl)-amide of Formula I A 20 ml screw-cap vial was filled with the following solids: CuO (0.05 mmol, 4.0 mg), anhydrous CuCl$_2$ (0.05 mmol, 6.7 mg), K$_2$CO$_3$ (2.0 mmol, 277 mg), 3-difluoromethyl-1-methyl-1H-pyrazole-4-carboxylic acid amide (1.1 mmol, 193 mg) and 5-bromo-9-dichloromethylene-1,2,3,4-tetrahydro-1,4-methano-naphthalene (1.0 mmol, 304 mg). A magnetic stir bar was added, and the open vial was gently flushed with N$_2$. Dioxane (2 mL) was added, followed by N,N'-dimethylethylenediamine (0.45 mmol, 48 µl). The vial was sealed and placed into a preheated screening block at 130° C. Conversion was complete after 24 hours. The yield (HPLC-analysis) of the compound of formula I was 70%.

The reaction can be performed analogously using 5,9,9-trichloromethylene-1,2,3,4-tetrahydro-1,4-methano-naphthalene as starting material.

What is claimed is:
1. A process for the preparation of the compound of formula I

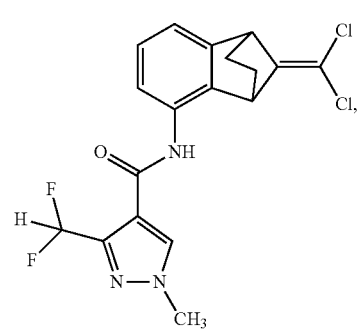

which process comprises
a) reacting a compound of formula II

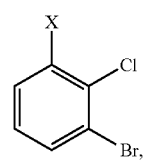

wherein X is chloro or bromo, with an organometallic species in an inert atmosphere to a halobenzyne of formula X

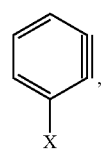

wherein X is chloro or bromo; reacting the halobenzyne of formula X so formed with cyclopentadiene to a compound of formula III

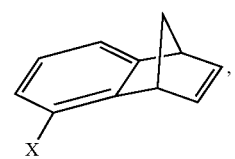

wherein X is chloro or bromo;
b) reacting the compound of formula III in the presence of an inert solvent with an oxidant to the compound of formula IV

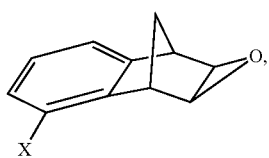

wherein X is chloro or bromo;
c) reacting the compound of formula IV in the presence of a Lewis acid and a hydride source to the compound of formula V

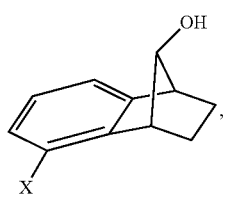
(V)

wherein X is chloro or bromo;
d) reacting the compound of formula V in the presence of an oxidizing agent, a base and an inert solvent to the compound of formula VI

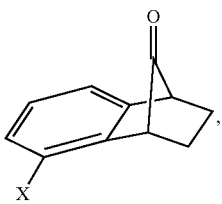
(VI)

wherein X is chloro or bromo;
e) converting the compound of formula VI in the presence of a phosphane and CCl$_4$ or CHCl$_3$ to the compound of formula VII

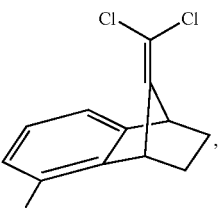
(VII)

wherein X is chloro or bromo; and either
f1) reacting the compound of formula VII with NH$_3$ in the presence of a catalyst comprising palladium and at least one ligand to the compound of formula VIII

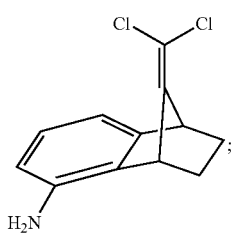
(VIII)

and g) reacting the compound of formula VIII in the presence of a base with a compound of formula IX

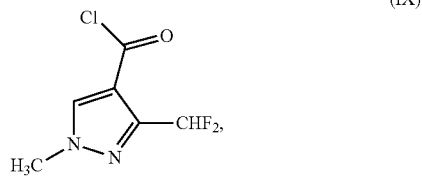
(IX)

to the compound of formula I; or
f2) reacting the compound of formula VII

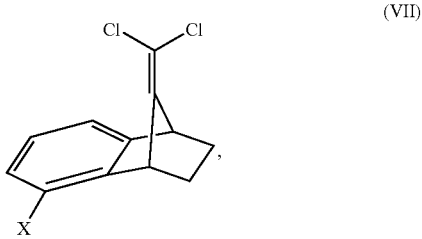
(VII)

wherein X is chloro or bromo; in the presence of a solvent, a base, a copper catalyst and at least one ligand with the compound of formula IXa

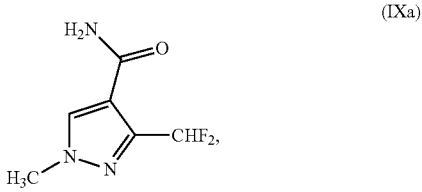
(IXa)

to the compound of formula I.

2. A process according to claim 1, which comprises
a) reacting a compound of formula II according to claim 1, wherein X is bromo, with a compound of formula III.

3. A process according to claim 1, wherein meta-chloroperbenzoic acid is used as oxidant in step b).

4. A process according to claim 1, wherein LiAlH$_4$ is used in step c) as the hydride source.

5. A process according to claim 1, which comprises reacting the compound of formula VII with NH$_3$ in the presence of a catalyst comprising palladium and at least one ligand to the compound of formula VIII

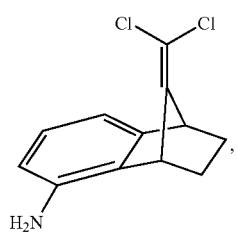

(VIII)

and reacting the compound of formula VIII in the presence of a base with a compound of formula IX

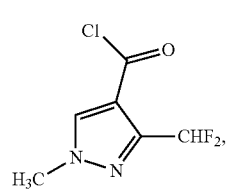

(IX)

to the compound of formula I.

6. A process according to claim 1, wherein in step e) the compound of formula VI is converted into the compound of formula VII in the presence of triphenylphosphane and carbontetrachloride.

7. The compound of formula IV

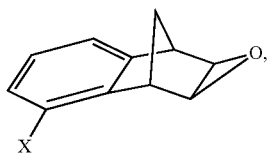

(IV)

wherein X is chloro or bromo.

8. The compound of formula V

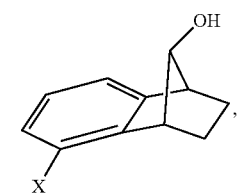

(V)

wherein X is chloro or bromo.

* * * * *